(12) United States Patent
Janssen

(10) Patent No.: US 11,386,995 B2
(45) Date of Patent: Jul. 12, 2022

(54) METHOD AND SYSTEM FOR CENTRALIZED PATIENT MONITORING MANAGEMENT

(71) Applicant: GE Precision Healthcare LLC, Wilmington, DE (US)

(72) Inventor: Brian D. Janssen, Brookfield, WI (US)

(73) Assignee: GE Precision Healthcare LLC, Wilmington, DE (US)

( * ) Notice: Subject to any disclaimer, the term of this patent is extended or adjusted under 35 U.S.C. 154(b) by 152 days.

(21) Appl. No.: 16/271,309

(22) Filed: Feb. 8, 2019

(65) Prior Publication Data
US 2020/0258622 A1    Aug. 13, 2020

(51) Int. Cl.
G16H 40/63    (2018.01)
G16H 40/20    (2018.01)
G08B 27/00    (2006.01)

(52) U.S. Cl.
CPC .......... *G16H 40/63* (2018.01); *G08B 27/001* (2013.01); *G16H 40/20* (2018.01)

(58) Field of Classification Search
CPC .................................................. G16H 40/20
See application file for complete search history.

(56) References Cited

U.S. PATENT DOCUMENTS

| 9,852,265 B1 | 12/2017 | Treacy et al. | |
|---|---|---|---|
| 2003/0149598 A1* | 8/2003 | Santoso | G06Q 10/10 705/2 |
| 2017/0098358 A1 | 4/2017 | Bechtel et al. | |

(Continued)

FOREIGN PATENT DOCUMENTS

| CN | 108399946 A | * | 8/2018 |
|---|---|---|---|
| GB | 2438757 | * | 6/2006 |

OTHER PUBLICATIONS

Machine Translation WO 2010/069190 A1 Hu, C., et al. (Year: 2009).*

(Continued)

*Primary Examiner* — Sheetal R Paulson
(74) *Attorney, Agent, or Firm* — Andrus Intellectual Property Law, LLP

(57) ABSTRACT

A method of centralized monitoring management at a centralized monitoring unit (CMU) includes receiving patient monitoring data from multiple patient monitoring devices, each providing patient monitoring data for one of multiple patients, and assigning each of the multiple patients to one of at least two monitoring technician stations. Each monitoring technician station is configured to receive and display patient monitoring data the patients assigned thereto and to present alarms for each patient to a CMU technician. A load index is calculated for each monitoring technician station based on the alarms for each patient in the group of patients assigned to that monitoring technician station. At least one patient is removed from the group of patients assigned to a first monitoring technician station of the at least two monitoring technician stations based on the load index for the first monitoring technician station. The patient removed from the first monitoring technician station is then reassigned to a different one of the at least two monitoring technician stations so as to distribute an overall alarm load for the CMU across all of the at least two monitoring technician stations.

23 Claims, 11 Drawing Sheets

(56) References Cited

U.S. PATENT DOCUMENTS

2017/0161443 A1    6/2017  Bassham
2017/0235910 A1    8/2017  Cantillon
2020/0228755 A1*   7/2020  Greco .................... H04N 7/181

OTHER PUBLICATIONS

PCT application PCT/US2020/016765 filed Feb. 5, 2020, International Search Report/Written Opinion dated Apr. 30, 2020, 14 pages.

* cited by examiner

Patient-specific alarms and activities detail

| Patient # | Alarm type | Escalations | Start | End | Total time |
|---|---|---|---|---|---|
| 234 | HR - low | 0 | 10:10:01 | 10:15:13 | 0:05:12 |
| 234 | Leads off | 1 | 10:45:16 | 10:57:35 | 0:12:19 |
| 234 | HR - low | 0 | 11:30:43 | 11:33:44 | 0:03:01 |
| 234 | Discharge | 0 | 13:54:03 | | |
| 345 | No telem | 1 | 8:15:56 | 8:18:22 | 0:02:26 |
| 345 | Asystole | 1 | 9:14:43 | 9:19:21 | 0:04:38 |
| 345 | HR - high | 1 | 10:11:21 | 10:17:17 | 0:05:56 |
| 456 | Admit | 0 | 9:12:09 | | |
| 456 | HR - high | 2 | 8:30:12 | 8:40:26 | 0:10:14 |
| 456 | IBP - high | 0 | 8:45:55 | 8:54:36 | 0:08:41 |
| 456 | SpO2 PR - high | 0 | 9:14:56 | 9:20:28 | 0:05:32 |
| 456 | SpO2 sat - low | 1 | 9:15:00 | 9:23:56 | 0:08:56 |
| 456 | RR - high | 0 | 9:25:17 | 9:30:10 | 0:04:53 |
| 567 | X-ray (transport) | 0 | | | |
| 567 | Afib | 0 | 9:17:13 | 9:26:29 | 0:09:16 |
| 567 | HR - high | 1 | 9:25:43 | 9:31:06 | 0:05:23 |
| 567 | NIPB - low | 0 | 9:26:13 | 9:26:13 | 0:00:00 |
| 567 | Afib | 0 | 9:45:48 | 9:56:00 | 0:10:12 |
| 567 | SpO2 sat - low | 1 | 9:54:17 | 10:01:00 | 0:06:43 |
| 567 | RR - high | 0 | 10:05:23 | 10:09:08 | 0:03:45 |
| 567 | Physical therapy | 0 | 10:50:20 | 12:08:20 | 1:18:00 |
| 567 | Shower | 0 | 12:32:10 | 12:56:10 | 0:24:00 |

FIG. 3A

| Alarm burden schedule | | | | | |
|---|---|---|---|---|---|
| Alarm type | Type (tech-arry-limit) | Severity | Response / support complexity | Call requirements | Expected response duration | Documentation (time est.) |
| Afib | Arry | M | L | No | 5 | 2 |
| Asystole | Arry | H | H | Yes | 5 | 10 |
| HR - high | Limit | L | L | No | 3 | 2 |
| HR - low | Limit | L | L | No | 3 | 2 |
| IBP - high | Limit | L | L | No | 3 | 2 |
| NIPB - low | Limit | L | L | No | 3 | 2 |
| V brady | Limit | M | M | Yes | 5 | 5 |
| v-tech | Limit | H | H | Yes | 7 | 10 |
| Leads off | Tech | H | M | Yes | 7 | 2 |
| No telem | Tech | H | M | Yes | 7 | 2 |
| Battery low | Tech | M | L | No | 5 | 2 |

| Activities burden schedule | | | | | |
|---|---|---|---|---|---|
| Care activity type | Number of interfaces | Response / support complexity | Call requirements | Expected response duration | Documentation (time est.) |
| Admit | 2 | L | No | 5 | 5 |
| Discharge | 3 | M | Yes | 10 | 10 |
| Return / clean equipment | 1 | L | No | 3 | 5 |
| Physical therapy | 1 | L | No | 3 | 0 |
| Shower | 1 | L | No | 3 | 0 |
| X-ray (transport) | 1 | L | No | 3 | 0 |
| Documentation (q4/patient) | 0 | L | No | 3 | 5 |

FIG. 3B ns. FIG. 1 depicts one exemplary embodiment of a centralized monitoring unit (CMU) 30 in communication with and receiving patient monitoring data, including alarm-related data, from multiple patient monitoring devices 16. In the depicted embodiment in FIG. 1, the CMU 30 receives patient monitoring data from multiple patient monitoring devices 16 monitoring multiple different patients 3 at two medical facilities 18a and 18b. In certain embodiments, the CMU 30 may be associated with and receiving patient monitoring data from patient monitoring devices 16a-16c within one medical facility 18, such as a hospital 18a. In such an embodiment, the CMU 30 may be located within the medical facility 18 or may be located remotely. In other embodiments, the CMU 30 may receive patient monitoring data from patient monitoring devices 16 at multiple medical facilities, such as from multiple hospitals, outpatient facilities, medical clinics, etc. within a hospital or provider

METHOD AND SYSTEM FOR CENTRALIZED PATIENT MONITORING MANAGEMENT

BACKGROUND

The present disclosure generally relates to patient monitoring, and more specifically to methods and systems for centralized patient monitoring management at a centralized monitoring unit (CMU) receiving patient monitoring data from patient monitoring devices for multiple different patients throughout a medical facility or throughout multiple medical facilities.

SUMMARY

In one embodiment, a method of centralized monitoring management at a centralized monitoring unit (CMU) includes receiving patient monitoring data from multiple patient monitoring devices, each providing patient monitoring data for one of multiple patients, and assigning each of the multiple patients to one of at least two monitoring technician stations. Each monitoring technician station is configured to receive and display patient monitoring data the patients assigned thereto and to present alarms for each patient to a CMU technician. A load index is calculated for each monitoring technician station based on the alarms for each patient in the group of patients assigned to that monitoring technician station. At least one patient is removed from the group of patients assigned to a first monitoring technician station of the at least two monitoring technician stations based on the load index for the first monitoring technician station. The patient removed from the first monitoring technician station is then reassigned to a different one of the at least two monitoring technician stations so as to distribute an overall alarm load for the CMU across all of the at least two monitoring technician stations.

A CMU receiving patient monitoring data from multiple patient monitoring devices includes at least two monitoring technician stations and an assignment management module. Each monitoring technician station is configured to receive and display patient monitoring data for each patient in a group of patients assigned thereto and to present alarms for each patient in a group of patients to the CMU technician. The assignment management module is executable by a processing system to calculate a load index for each monitoring technician station. At least one patient of the multiple of patients assigned to a first monitoring technician station is removed based on the load index for the first monitoring technician station. The at least one patient removed from the first monitoring technician station is then reassigned to a different one of the at least two monitoring technician stations.

Various other features, objects, and advantages of the invention will be made apparent from the following description taken together with the drawings.

BRIEF DESCRIPTION OF THE DRAWINGS

The drawings illustrate the best mode presently contemplated of carrying out the disclosure. In the drawings:

FIG. 3A illustrates an exemplary list of alarm activity over a period of time for an exemplary group of patients assigned to a CMU technician.

FIG. 3B illustrates exemplary schedules for calculation of burden values associated with alarm types and care activity types.

DETAILED DESCRIPTION

Figure 1:
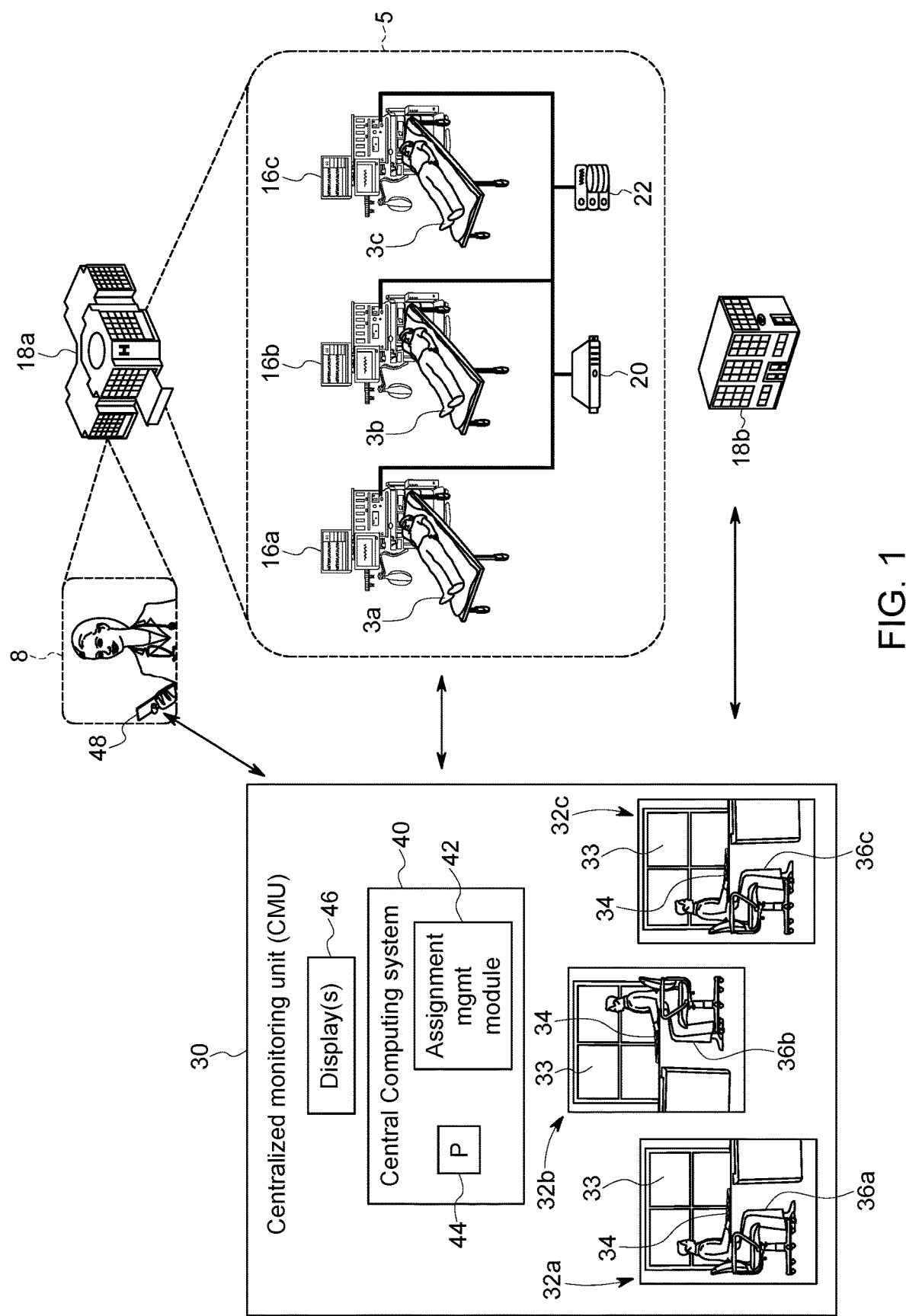
FIG. 1 schematically depicts an exemplary embodiment of a centralized monitoring unit receiving patient monitoring data from patient monitoring devices in multiple medical facilities.

Medical device alarms are helpful to draw clinician attention to alarms, which may regard technical issues with the patient monitoring arrangement or devices or a physiological event detected in the physiological data recorded from that patient. However, given the number of patient monitoring devices and other care devices that generate alarms, often simultaneously, alarm response can overburden and overwhelm clinicians and present a barrier to effectively managing and responding to alarms, some of which are for critical health-related emergencies. If too many alarms are initiated, clinicians are likely to suffer from alarm fatigue and, if auditory alarms are generated, patients hearing the alarms are likely to become agitated.

Accordingly, there is a need for an effective monitoring management system capable of receiving and processing patient monitoring data and alarm information and to determine which alarms are in need of response by a clinician. In one embodiment, a centralized monitoring unit (CMU) receives patient monitoring data from multiple patient monitoring devices connected to multiple different patients and facilitates assessment of alarms for each patient by a CMU technician. The CMU technician assesses the alarm, such as to determine whether the alarm warrants a visit from a clinician to the patient and then facilitates notification of the alarms to a responding clinician. The inventor has recognized that in such a CMU, technicians may also become overburdened, especially where the CMU technician may be assigned to a group of patients that is generating an especially high number of alarms or especially burdensome or critical alarms. Accordingly, the inventor has recognized that systems and functions are needed for workload management amongst CMU technicians working at monitoring technician stations in a CMU, including workload estimation, resource assessment, and load balancing.

network. Within a medical facility 18a, 18b, the patient monitoring devices 16 may be located in a plurality of medical care units. Each medical care unit may be specific to a particular type of care. Non-limiting examples of medical care units include, but are not limited to, medical telemetry units, step down units, emergency rooms, intensive care units, specialty intensive care units (e.g., cardiovascular ICU), neonatal and/or pediatric care units, postoperative care units, etc.

The CMU 30 includes two or more monitoring technician stations (MTSs) 32 (e.g., 32a-32c). The CMU 30 may receive patient monitoring data from any number of two or more patient monitoring devices 16a-16c collecting and monitoring physiological data from patients 3a-3c. Each patient 3a-3c is assigned via the CMU 30 to one of the MTS 32a-32c such that each MTS 32a-32c has an assigned group of patients for which it facilitates monitoring by a respective CMU technician 36a-36c. In another embodiment, a monitoring technician 36 may manually admit a patient to their station, such as seeing that a new patient needs assignment and manually accepting assignment to their respective MTS 32a-32c. The patient monitoring device 16a-16c may be any device collecting and/or assessing physiological data from the patient 3a-3c. Examples include an electrocardiograph (ECG), non-invasive blood pressure monitor (NIBP), invasive blood pressure monitor, Sp02 monitor, electroencephalograph (EEG), respiration monitor, or any other monitoring device capable of collecting physiological or other patient monitoring data. As is common, multiple patient monitoring devices may be connected to each patient 3a-3c. The patient monitoring data from each patient monitoring device 16a-16c is transmitted to the CMU 30, such as via the computer network of the medical facility 18a and/or the internet.

A CMU technician 36 operates each MTS 32 in order to review patient monitoring data and assess alarms from multiple different patients (e.g., 3a-3c). The CMU technician 36 assess the patient monitoring data from patient monitoring devices 16 for each patient 3 in a group of patients admitted or assigned to the CMU technician's MTS 32. With reference to the example in FIG. 1, the first MTS 32a may be configured to receive and display patient monitoring data for each patient 3a-3c in a group of patients 5 assigned thereto, and present alarms for each patient 3a-3c in the group of patients 5 to the CMU technician 36a. The CMU technician 36a then assesses the patient monitoring data associated with each alarm. In certain embodiments, an alarm notification may also be sent automatically to the caregiver or care team via a secondary alarm notification system; however, in most cases, the technician 36a will still need to conduct some level of assessment. For example, the CMU technician 36a assesses the patient monitoring data to determine whether the alarm is one that needs to be responded to by a responding clinician or technician, or whether the alarm is a false alarm (e.g., caused by a noisy signal) or otherwise does not require a visit to the patient's location by a clinician (to physically assess and/or treat the patient) or technician (to assess the patient monitoring device and/or sensors attached to the patient).

The CMU 30 includes a central computing system 40 comprising an assignment management module 42, which is a software module comprising computer executable instructions for managing workload assignments to the two or more monitoring technician stations 32a-32c. Each monitoring technician station (MTS) 32a-32c comprises one or more display(s) 33 that visually present patient monitoring data for various patients to a CMU technician 36a-36c. Each MTS 32a-32c further includes one or more user input devices 34 through which the CMU technician can input information and/or navigate the central monitoring user interface provided on the graphical display(s) 33. Each CMU technician 36a-36c assesses the patient monitoring data relevant to each alarm and documents, where appropriate, the assessment via the user input devices at the MTS 32, such as a mouse, keyboard, touchpad, touchscreen, voice recognition system, or any other standard or non-standard user input device or system. Alternatively, the documentation could be conducted on paper.

In one embodiment, each MTS 32a-32c includes its own computing system that is communicatively connected to the central computing system 40 and runs the displays 33 and receives input from the user input devices 34 in order to facilitate the functions of the CMU technician 36a-36c operating the respective MTS 32a-32c. Alternatively, each MTS 32a-32c may operate on the central computing system 40, which may be configured to run multiple instances of the centralized monitoring user interface—e.g., a cloud computing environment.

Each MTS 32 is configured to facilitate assignment of alarm response or other patient treatment or assessment to at least one responding clinician 8, which may be a care team comprised of more than one clinician. For example, the CMU technician 36 may operate the centralized monitoring user interface provided at the MTS 32 to link a responding clinician 8 to an alarm for a patient. The centralized monitoring user interface may facilitate communication between the CMU technician 36 and the responding clinician 8, such as by allowing text and/or voice communication between each MTS and a clinician device 48, such as a smart phone or other personal computing device. For example, the clinician device 48 may be a personal computing device running an application to provide the centralized monitoring user interface(s) that facilitates communication of alarm assignments to that clinician 8 and/or communication between the clinician 8 and the CMU technician 36 regarding the assignment, the patient condition, and/or whether the clinician 8 is able to respond to the alarm assignment. For example, the clinician 8 may utilize the clinician device 48 to accept or deny the alarm dispatched, and the acceptance or denial may be communicated to the CMU technician at the corresponding MTS 32a-32c. If the clinician 8 denies the dispatched alarm, then the CMU technician 36 may assign the alarm to a different responding clinician or be automatically escalated to another assigned clinician such as via an integrated secondary alarm notification solution. Once made, each responding clinician assignment may stay with each patient, regardless of any transfer of patients or patient groupings among MTSs 32a-32c. Thus, the notifications for alarm responses for a particular patient may move with the patient automatically when the patient gets reassigned to a different MTS 32a-32c such that the notifications continue to be routed to the same responding clinician or group of clinicians.

Figure 2:
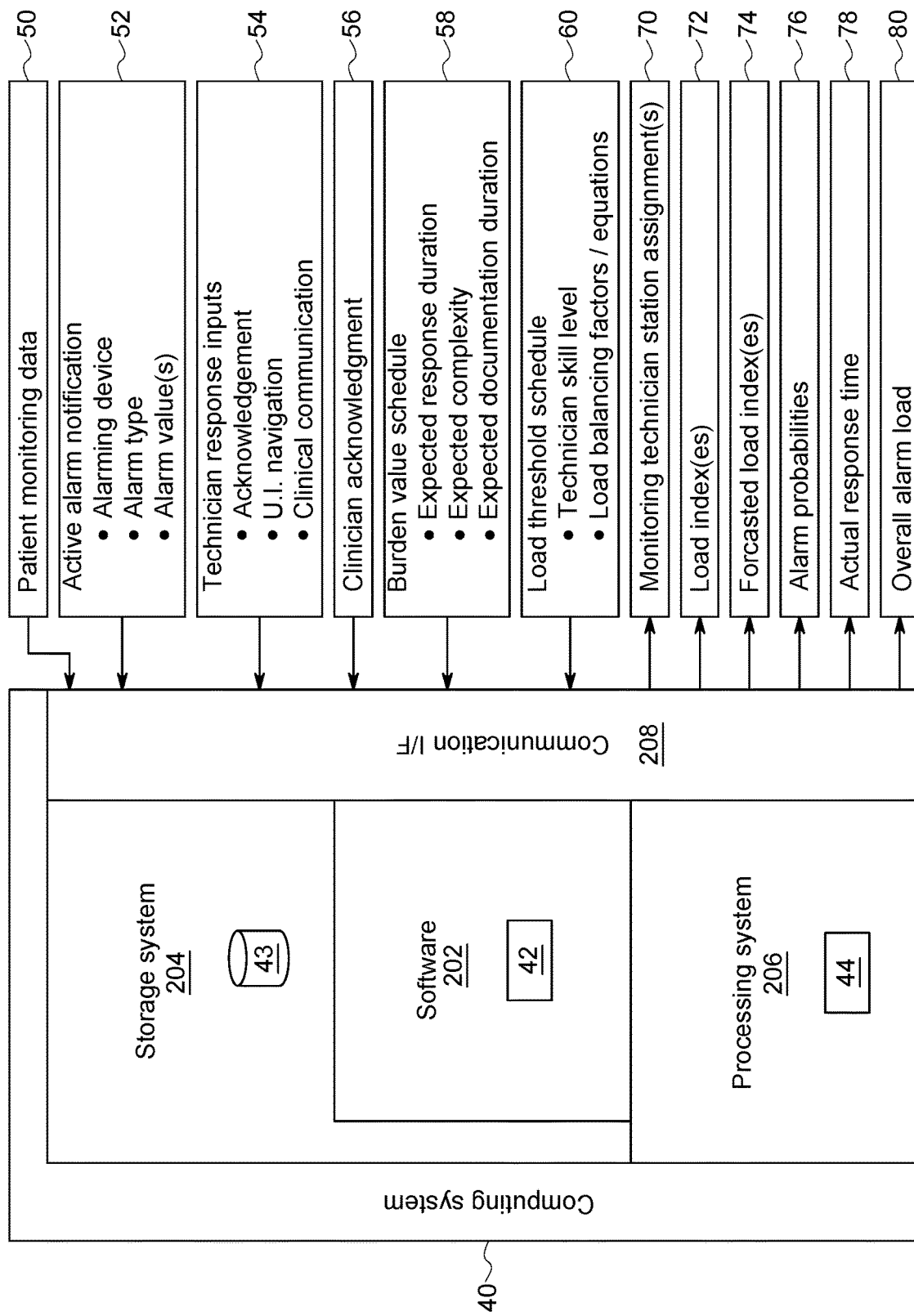
FIG. 2 is a block diagram representing a central computing system having an assignment management module executable to perform load management functions as described herein.

Each of the patient monitoring devices 16 are exemplarily communicatively connected by a local network which may be operated by a local server 20 which may exemplarily handle and process the data from each of the patient monitoring devices 16 in an area, such as in a hospital or care unit. In an exemplary embodiment, wherein the CMU 30 is implemented at a single hospital or other location, the local server 20 may be in direct communication with the central computing systems 40. In a more distributed or cloud-based implementation, a communications gateway 22 may communicatively connect the local server 20 to the central computing system 40 of the CMU 30. As also illustrated in FIG. 2, the central computing system 40 exemplarily receives alarm data 52 and patient monitoring data 50 for each of the patient monitoring devices 16 exemplarily through at least one of the local server 20 and the communications gateway 22 and makes the data accessible to the assigned CMU technician 36a-36c via the corresponding MTS 32a-32c.

Each patient 3a-3c for which patient monitoring data is being received is assigned to one of the MTSs 32a-32c for review by the respected CMU technician 36a-36c manning that MTS. Thus, each MTS 32a-32c has a group of two or more patients 3a-3c assigned thereto. In FIG. 1, a representative group 5 of patients 3a-3c is assigned to a first one of the MTSs 32a, other groups of patients (not shown) are assigned to each of the other two MTSs 32b-32c. The multiple patients 3 being monitored may be divided and assigned amongst the groups 5 assigned to the various MTS 32a-32c by various methods described herein. As also described hereinbelow, the assignment of patients to the MTSs 32a-32c is continually managed so that the workload for all of the patients being monitored at the CMU 30 is distributed across all of the MTS 32a-32c in an effective and equitable manner so that no single CMU technician 36a-36c is overburdened compared to other technicians and so that all alarms can be assessed in the most prompt and efficient manner possible.

The assignment management module 42 operates as described herein to calculate a load index for each MTS 32a-32c and redistribute patient assignments to the various MTS 32a-32c based on the load indexes and the active alarms so as to efficiently and effectively distribute an overall alarm load for the CMU 30 across all of the MTSs 32a-32c operated by a CMU technician 36a-36c. Thus, while a patient may be initially assigned to a particular monitoring technician station 32a-32c upon intake, that assignment may change over time based on the overall alarm load and/or based on loading at any particular MTS 32a-32c. In one example, a patient may be initially assigned to a monitoring technician station 32a-32c that has the lowest load index at the time of assignment, such as upon intake of the patient or upon receipt of initial monitoring data for that new patient. Alternatively, the initial assignment or admission may be based on the expertise of the monitoring technician 36a-36c manning each respective MTS 32a-32c. The initial assignment of a new patient to an MTS 32a-32c may be performed automatically by the assignment management module 42, such as based on the current load indexes based on the current assignments, or suggest the MTP to which to assign the patient for confirmation by a system manager or administrator overseeing assignment prior to executing the assignment. The continual monitoring for that patient over time may then be transferred to various MTSs 32a-32c based on a load index for each MTS 32a-32c, a forecasted load index for each MTS 32a-32c, an overall alarm load for the CMU 30, particular skill levels and/or expertise of CMU technicians 36a-36c (who may change shifts, etc.), or any other various factors disclosed herein.

In one embodiment, the CMU 30 houses an assignment management module 42 comprising computer executable instructions housed in software 202 and executable by one or more processors 44 comprised in a processing system 206. As shown in the system diagram of FIG. 2, the assignment management module 42 is configured to receive patient monitoring data 50 and various other inputs and schedules and to calculate load indexes 72, one for each MTS 32 of the CMU 30, and to make MTS assignments 70 of patients 3 to each MTS 32 in order to distribute an alarm load for the CMU 30. In the depicted example, the assignment management module 42 receives active alarm notifications 52 for each patient 3 being monitored at one of the MTSs 32. The active alarm notification 52 identifies one or more of the alarming device and type of alarm, and may also identify the physiological measurement values that triggered the alarm, especially for limit alarms (see FIG. 5B and associated discussion below). The active alarm notification 52 may also identify a patient 3a with which the alarm is related. The assignment management module 42 then calculates a load index 72 for each MTS 32 based on the active alarms being handled there. In certain embodiments, the load index 72 for each MTS 32 may be calculated based further on technician response inputs 54 by the CMU technician at the respective MTS 32. The technician response inputs 54 may include acknowledgments of an active alarm and other inputs to the centralized monitoring user interface at the respective MTS 32 for assessment of an active alarm, such as to review patient monitoring data for the patient and/or patient health or other related information considered as part of the alarm assessment. For example, the technician response inputs 54 may include window or button selections, information input, etc. via the user input device(s) 34 at the MTS 32. Such information may be tracked in order to determine what review and response actions have been taken by the CMU technician 36.

The technician response inputs 54 may further include clinician communication, such as communication with a responding clinician 8 or responding technicians, and/or consultation with other clinicians, technicians, or subject matter experts. Such information may be considered when calculating the load index 72, such as to determine an actual response time 78—i.e., an actual amount of time that responding to a particular alarm has consumed. In certain embodiments, the load index 72 may also be calculated based on the total duration of continuous alarming experienced at the MTS 32, which is the total time that alarms have been continuously handled by the CMU technician 36 without time therebetween or with less than a predetermined amount of time between alarms.

Additionally, the actual response time 78 can be compared to an expected response duration, such as determined based on alarm type. For example, an expected response duration may be provided in one or more burden value schedules 58. Burden value schedules 58 (exemplified at FIG. 3B) provide expected response information for each of various alarm types that could be generated by the patient monitoring devices 16 providing patient monitoring data 50 to the CMU 30. For example, the burden value schedule 58 may provide an expected response duration for each alarm type listing an expected amount of time required to assess an active alarm, determine whether a clinician response is needed, and hand off the matter to a responding clinician 8. The burden value schedule 58 may further identify an expected complexity of an alarm type, such as to represent how much attention and energy will be required by the CMU technician 36 to assess and/or assign an active alarm of the particular alarm type. Additionally, the burden value schedule 58 may specify an expected documentation duration by alarm type, such as to specify a duration required to complete documentation of the technician's assessment and assignment and/or document any other information relevant to an alarm. For example, the expected documentation duration may represent the period of time required after assignment of an alarm to a responding clinician 8 and/or determination that no clinician response is necessary and silencing or termination an alarm condition.

The assignment management module 42 may consider the burden value schedule 58 when calculating the load index 72 for each MTS 32, such as to determine a burden value for each active alarm being addressed at the MTS 32, which is based on the type of each respective alarm and indicates the estimated burden on the CMU technician 36 caused by each respective alarm. In certain embodiments, the assignment management module 42 may be configured to further assess a load threshold schedule 60 in determining the load index and/or determining a load threshold for each individual MTS 32 to which the respective load index should be compared. For example, the load threshold schedule 60 may list information regarding the skill level of the CMU technician 36 at the respective MTS 32. The skill level information may be used in various ways. For example, the skill level information may be utilized to modify the information in the burden value schedule 58. For example, a multiplier may be provided to information in the burden value schedule 58 based on the technician skill level to account for the varied abilities of the technicians (e.g., 36a-36c) who may be responding to alarms. For example, an inexperienced technician may take longer to assess and respond to an alarm and the complexity of their response may increase, such as due to the need to consult with another technician and/or a subject matter expert. Conversely, an experienced technician may be able to assess and respond to an alarm condition more quickly and efficiently. Thus, the burden value calculated for an inexperienced technician may be higher than for an experienced technician for the same alarm type.

Figure 10:
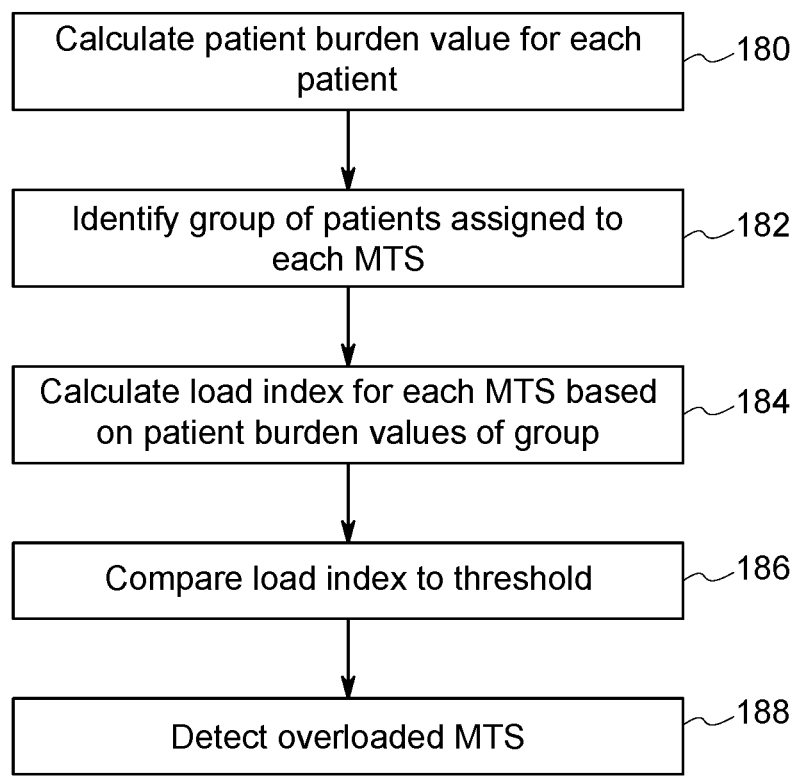

In one embodiment, a patient burden value may be calculated for each patient, and the assignment management module 42 may then calculate the load index 72 for each MTS 32 as the total of the patient burden values for the patients assigned thereto. FIG. 10 is a flow chart illustrating one such example where load index 72 is calculated based on patient-specific values. A patient burden value is calculated for each patient at step 180. The patient burden value may be calculated based on an alarm burden schedule as described herein. Referencing FIG. 3A as an example, a burden value may be calculated for each patient (e.g., patient 234, patient 345, etc.) based on the listed activity for that patient and using appropriate burden schedules. Then, based on the group of patients for each MTS 32 identified at step 182, a load index is calculated at step 184. The load index 72 for a respective MTS 32 is determined based on the patient burden values, such as the sum of the patient burden values for the group of patients 5 assigned to a particular MTS 32. The load index 72 is then compared to a threshold at step 186 to identify whether there are any overloaded MTSs 32. Based on the MTS load indexes, the assignment management manager may then determine and provide, through optimization algorithms, reassignment recommendations, balancing the load levels of the MTSs in the CMU.

The technician skill level may be utilized to calculate a load threshold for each technician to which the load index is compared. For example, an inexperienced CMU technician 36 may be assigned a lower load threshold than an experienced technician. In certain embodiments, the load index 72 calculated for each MTS 32 may be compared to the load index assigned to the CMU technician 36 working at that MTS 32. If the load index 72 exceeds the respective load threshold, then that MTS 32 may be identified as an overloaded MTS indicating a need for reassignment of one or more patients in order to adjust the alarm load distribution.

The load threshold schedule 60 may further include other load balancing factors and/or equations, such as to account for various considerations when assigning burden value for each active alarm and/or load threshold for each CMU technician 36. Examples of additional load balancing factors could include modifiers to account for factors such as clinician fatigue (e.g., to lighten a load on a clinician after a period of high stress or high load). Alternatively or additionally, the load threshold schedule 60 may include equations and/or other information on how to balance an overall alarm load across all MTS 32a-32c of the CMU 30. Additional factors may be considered in addition to load index 72, such as the differences between load indexes amongst the various MTS 32a-32c. For example, the load threshold schedule 60 may include a threshold difference between load indexes 72 that may also trigger a load rebalancing.

Load rebalancing may further account for forecasted values indicating future load, and thus rebalancing may occur prior to a load index 72 exceeding a load threshold. For example, the assignment management module 42 may calculate a forecasted load index 74 for each MTS 32. The forecasted load index may account for any of several factors, including an actual response time 78 and/or technician response inputs 54. For example, a technician may indicate that a response will exceed the expected response duration and/or has an unusually high complexity based on the particular alarm type. The load index 72 or forecasted load index 74 may be modified upwards accordingly, alternatively or additionally, the forecasted load index 74 may account for alarm probabilities 76, which indicate the probability of an alarm being generated within a predetermined future time period based on the patient monitoring data 50 or related patient information. For example, alarm probabilities 76 may be increased for certain monitoring devices as the monitored values approach an alarm limit. Alternatively or additionally, alarm probabilities 76 may be increased for a particular patient or patient monitoring device 16 based on the other active alarms for that patient 3 and/or based on patient information such as diagnosis or medical history. For example, a critical ECG alarm may be closely followed by alarms generated by other patient monitoring devices, such as blood pressure and/or SpO2. Accordingly, high alarm probability values may account for those subsequent alarms, which may be reflected in the forecasted load index 74 for a particular MTS 32. Similarly, certain alarms may be more likely in predefined conditions for patients with certain diagnoses or medical histories. The alarm probability 76 may account for such information, and thus may increase when those predefined conditions or patterns are detected.

In certain embodiments, the assignment management module 42 may also receive or calculate an overall alarm load 80 representing the alarm load across all MTS 32a-32c. In one example, the overall alarm load 80 is a total of all load indexes 72 for the current operating MTS 32a-32c for the CMU 30. In another embodiment, the overall alarm load 80 may be determined based on the load indexes 72, and in some embodiments also the forecasted load indexes 74. In certain embodiments, the assignment management module 42 may be configured to account for the overall alarm load 80 for the CMU 30, such as to ensure that the load is not inequitably distributed to otherwise carried more by certain CMU technicians 36 may in others.

In one embodiment, the load determination is made based on burden value schedules indicating factors to be accounted for when assessing load. FIG. 3B depicts exemplary burden value schedules 58 providing a non-exhausted list of alarm types and other care activity types that a CMU technician 36 might engage in such that most or all of the demands on the CMU technician are accounted for in the load index 72 calculation. Each alarm type and/or activity type is associated with various information that may be considered in determining the burden value for each active alarm. In the depicted example, the burden schedules list an expected response duration and an expected documentation duration for each alarm type. In certain embodiments, the burden value schedules 58 may further contain an expected complexity value and/or allow calculation of an expected complexity based on the values indicated therein. In the depicted example, each alarm type and care activity type is classified into one of three expected complexity values, being low, medium, and high. Higher complexity values can be reflected in a higher burden value associated with the alarm type.

In various embodiments, the burden value schedules 58 may be configured and provided upon installation of a CMU 30 and maintained and updated as part of system maintenance. Alternatively or additionally, the schedules may be configurable, such as by a system administrator for the CMU 30. Thus, the burden value schedules 58 may be adjusted to account for particular realities in the healthcare environment in which the CMU 30 is operated. In still other embodiments, the assignment management module 42 may be configured to automatically adjust the burden value schedules 58 based on actual occurrences and operation at the CMU 30. For example, the assignment management module 42 may employ machine learning algorithms to update the burden schedules 58, such as to update the expected response durations and/or expected documentation duration values in the burden schedule based on actual response times 78 for the various alarm types and actual documentation durations. Likewise, the complexity values may be updated, such as based on the technician response inputs 54 measured for certain alarm types compared to the expected response inputs reflected in the burden value schedule 58. In certain embodiments, machine learning may be employed to maintain a burden value schedule 58 for each CMU technician 36a-36c, such as to accurately predict the response and documentation times for that technician, and thus more accurately predicts the amount of load that the respective technician 36a-36c can effectively handle.

FIG. 3A provides an exemplary list of alarm activity detail for a group of patients 5 assigned to a particular MTS 32. In the example, the group of patients 5 consists of four patients, identified as patient 234, patient 345, patient 456, and patient 567. In the example, a number of alarms are generated for each patient. The alarm activity schedule lists various alarm notification information 52, including alarm type and alarm start time. Certain additional information is also provided summarizing certain activity totals for each alarm event, including the total alarm time and the number of alarm escalations, which represent the number of persons, such as responding clinicians or technicians 8, who were called in or tasked to respond to the alarm. Such escalation information and total time information may be utilized, for example, by the machine learning algorithm to modify the burden schedule 58, which may be on a per-alarm-type basis and/or on a per-technician basis.

FIG. 2 is a block diagram representing an exemplary central computing system 40 of a CMU 30 having an assignment management module 42 executable to operate as described herein. The central computing system 40 includes a processing system 206, storage system 204, software 202, and a communication interface 208. The processing system 206 loads and executes software 202 from the storage system 204, including the assignment management module 42, which is an application within the software 202. The module 42 includes computer-readable instructions that, when executed by the computing system 40 (including the processing system 206), direct the processing system 206 to operate as described in herein in further detail, including to determine the load index 72 for each MTS 32 and to manage the load distribution among the MTSs 32 accordingly.

Although the central computing system 40 as depicted in FIG. 2 includes one software 202 encapsulating one assignment management module 42, it should be understood that one or more software elements having one or more modules may provide the same operation. Similarly, while description, as provided herein, refers to a single processing system 206 having a single processor 44, it is to be recognized that implementations the processing system 206 can be performed using one or more processors, which may be communicatively connected, and such implementations are considered to be within the scope of the description.

The processing system 206 includes the processor 44, which may be a microprocessor, a general purpose central processing unit, an application-specific processor, a microcontroller, or any other type of logic-based device. The processing system 206 may also include circuitry that retrieves and executes software 202 from storage system 204. Processing system 206 can be implemented within a single processing device but can also be distributed across multiple processing devices or sub-systems that cooperate in executing program instructions.

The storage system 204, which stores the database 43 housing various schedules 58, 60 and information necessary to facilitate the assignment management and load balancing activities by the assignment management module 42, can comprise any storage media, or group of storage media, readable by processing system 206 and capable of storing software 202. The storage system 204 can include volatile and non-volatile, removable and non-removable media implemented in any method or technology for storage of information, such as computer-readable instructions, data structures, program modules, or other data. Storage system 204 can be implemented as a single storage device but may also be implemented across multiple storage devices or sub-systems. For example, the software 202 may be stored on a separate storage device than the database 43 housing the schedules 58, 60. Likewise, database 43 can be stored, distributed, and/or implemented across one or more storage media or group of storage medias. Similarly, database 43 may encompass multiple different sub-databases at different storage locations and/or containing different information which may be stored in different formats. Storage system 204 can further include additional elements, such a controller capable of communicating with the processing system 206.

Examples of storage media include random access memory, read-only memory, optical discs, flash memory, virtual memory, and non-virtual memory, magnetic sets, magnetic tape, magnetic disc storage or other magnetic storage devices, or any other medium which can be used to store the desired information and that may be accessed by an instruction execution system, as well as any combination or variation thereof, or any other type of storage medium. Likewise, the storage media may be housed locally with the processing system 206 or may be distributed in one or more servers, which may be at multiple locations and networked, such as in cloud computing applications and systems. In some implementations, the storage media can be a non-transitory storage media. In some implementations, at least a portion of the storage media may be transitory.

The communication interface 208 interfaces between the elements within the central computing system 40 and external devices, such as the communications gateway 22 at various medical facilities 18a, 18b in order to receive patient monitoring data 50 and/or active alarm notification data 52. The communication interface 208 may also interface with the computing systems of the MTSs 32a (which in certain embodiments described above, may each comprise its own computing system or in other embodiments may all be facilitated in a cloud computing environment).

The central computing system 40 may be associated with a user interface, such as for receiving input from and communicating information to a system administrator. For example, the central computing system 40 may be associated with one or more displays 46, which may display various dashboards and/or other display tools indicating various statistics and information about the current load indexes 72 of the MTSs 32 and the overall alarm load 80 or load distribution status for the CMU 30. Each user interface for the central computing system 40 (as well as each user interface for each MTS 32) may include a mouse, a keyboard, a voice input device, a touch input device for receiving a gesture from a user, a motion input device for detecting non-touch gestures and other motions by a user, and other comparable input devices and associated processing elements capable of receiving input from a user, such as a clinician. Output devices such as video displays can display an interface further associated with embodiments of the system and method as disclosed herein. Speakers, printers, haptic devices and other types of output devices may also be included in the user interface.

Figure 4:
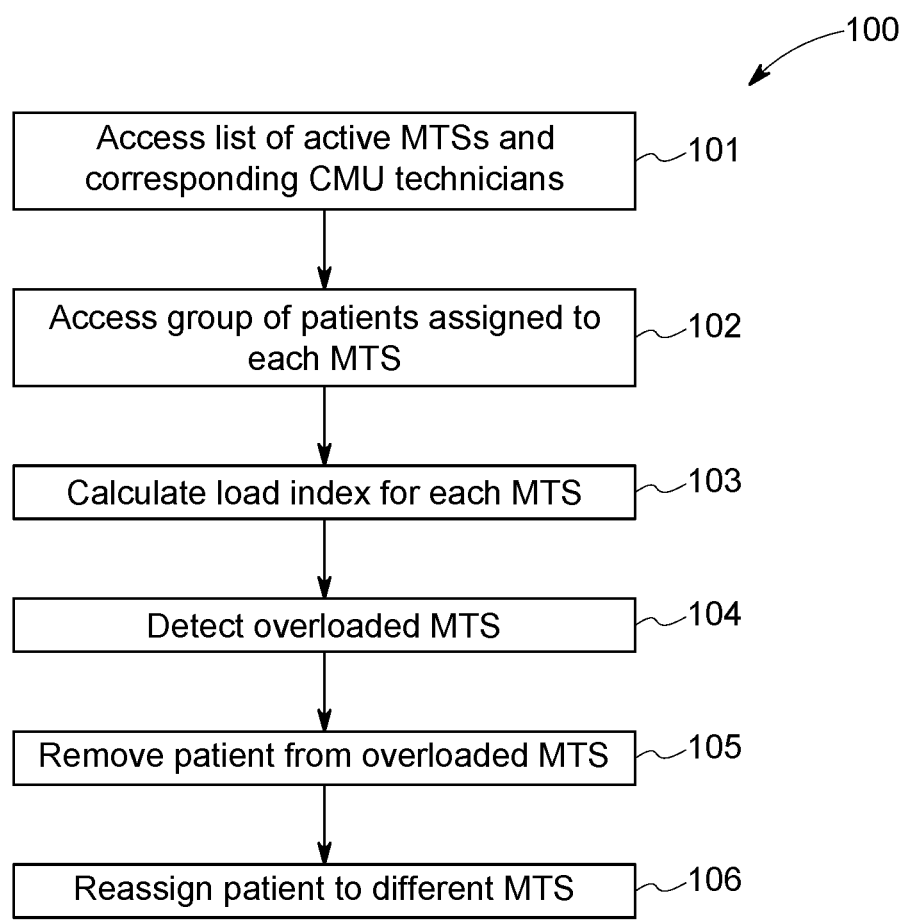
FIGS. 4-10 depict various embodiments of methods, or portions thereof, of centralized patient monitoring management at a CMU.

FIGS. 4-9 provide flowcharts exemplifying embodiments of methods 100, or portions thereof, of centralized patient monitoring management at a CMU 30. FIG. 4 depicts one exemplary method at a high level, where a load index is calculated and an overall alarm load is redistributed accordingly. At step 101, instructions are executed to access a list of active MTSs 32 and corresponding CMU technicians 36 assigned thereto. The group of patients assigned to each MTS is accessed at step 102, and a load index is calculated at step 103 for each MTS 32. Step 104 is executed to detect an overloaded MTS (e.g., 32a), after which at least one patient is removed from the overloaded MTS 32a at step 105 and reassigned to a different MTS 32b-32c at step 106—i.e., changing the MTS assignment 70 for that patient. A person having ordinary skill in the art will understand in view of the present disclosure that various methods may be employed for calculating the load index 72 and detecting an overloaded MTS. Likewise, a person having ordinary skill in the art will understand in view of the present disclosure that various algorithms may be employed to determine which patient or patients should be removed from the overloaded MTS, and where those patients should be reassigned. In certain embodiments, the reassignment may be executed automatically by the central computing system 40 upon detecting an overloaded MTS, in other embodiments the central computing system may seek approval input from on or more CMU technicians 36 or an administrator prior to executing the reassignment.

Figure 5A:
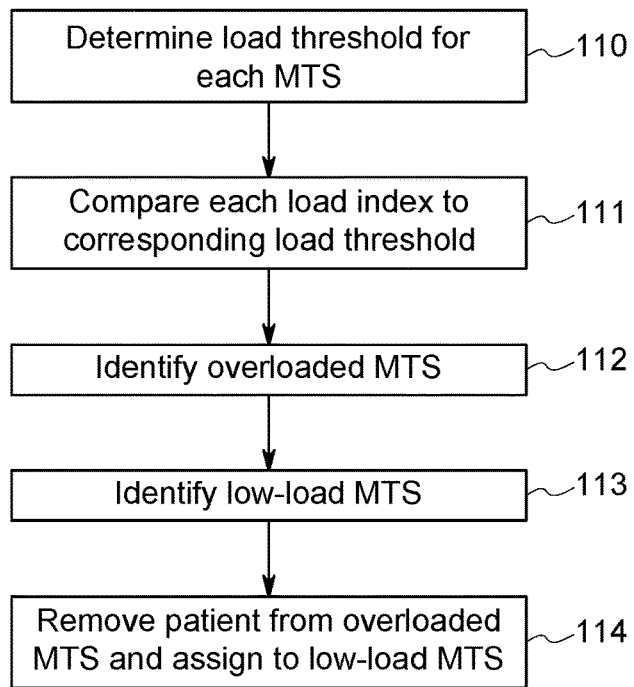
Figure 5B:
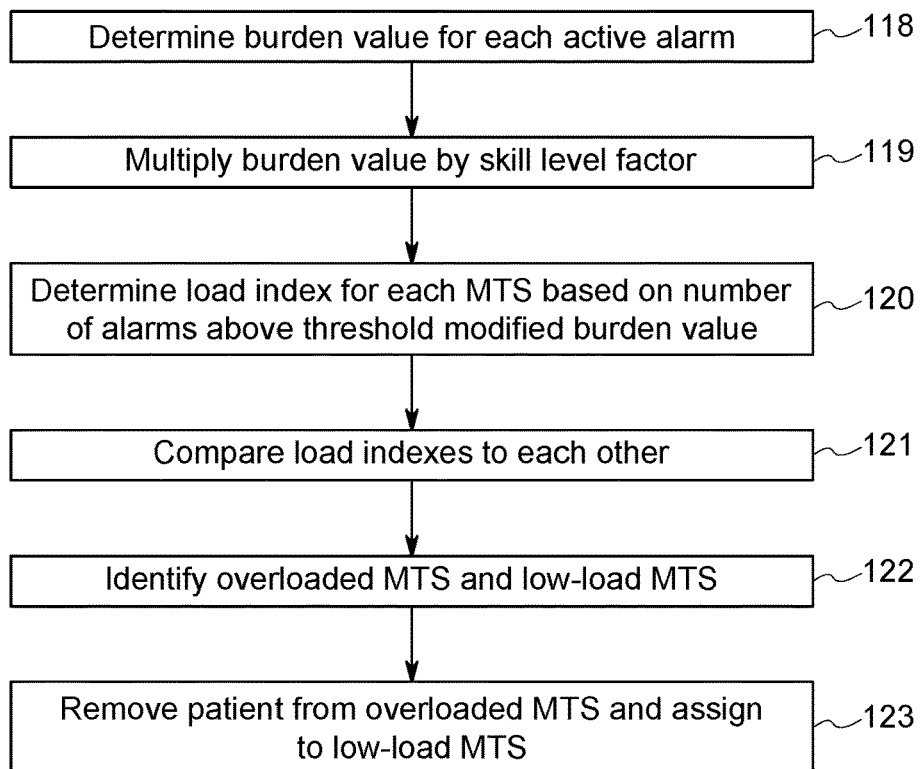

FIGS. 5A and 5B depict exemplary steps for identifying an overloaded MTS and a low-load MTS in order to adjust the distribution of patients among the MTS. In FIG. 5A, a load threshold is determined for each MTS 32a-32c at step 110. For example, the load threshold for each MTS 32a-32c may be determined and set based on skill level of the CMU technician 36a-36c at the respective MTS 32a-32c and/or other information contained in the load threshold schedule 60. The load index 72 calculated for each MTS 32 is compared to its corresponding load threshold at step 111. Overloaded MTS are identified at step 112 based on that comparison. For example, an overloaded MTS may be any MTS 32 for which the load index 72 meets or exceeds the respective load threshold determined for that MTS 32. One or more low-load MTSs are identified at step 113, such as the one or more MTSs with the largest difference between the load index and the load threshold for that MTS (where the load index is less than the load threshold). In certain embodiments, the low-load MTS may be identified based on a percentage basis, rather than an absolute value basis, to account for the variation in load thresholds between the CMU technicians 36a-36c. Instructions are then executed at step 114 to remove at least one patient from the overloaded MTS and assign that patient to the low-load MTS.

The exemplary method steps in FIG. 5B employ a different method of assessing load index and identifying overloaded MTS. A burden value is determined at step 118 for each active alarm, such as based on the alarm type of each active alarm and the burden value schedule 58. Step 119 is then executed to modify the burden value by the skill level of the technician, such as by multiplying the burden value calculated based on the burden value schedule 58 by a multiplier value determined based on the technician skill level from the load threshold schedule 60. In certain embodiments, the load index 72 may be assigned as the modified burden value for each alarm for all of the patients in the group of patients assigned to the MTS 32. Alternatively, the load index may be calculated to only account for the more serious and burdensome alarms being addressed at the MTS 32. In the exemplary embodiment of FIG. 5B, the load index is determined based on a number of alarms above a threshold modified burden value. Either way, the load index determined based on the modified burden value already accounts for the various skill levels of the technicians, and any other burden factors dictated by the load threshold schedule 60 discussed above. Thus, the load indexes for the various MTSs 32 can be directly compared to one another in order to determine whether the load distribution needs to be adjusted. For example, the assignment management module 42 may be configured to determine a mean load index and compare the load indexes 72 for each MTS 32 to the mean value in order to identify one or more overloaded MTS and one or more low-load MST, which is represented at step 122. For example, a threshold deviation from the mean may be set to account for natural and tolerable deviations in load. The overloaded MTS and low-load MTS may be identified as MTS with load indexes that deviate from the mean by more than the threshold amount or threshold percentage. At the point, one or more patients are removed from the overloaded MTS and assigned to the low-load MST at step 123.

Figure 6:
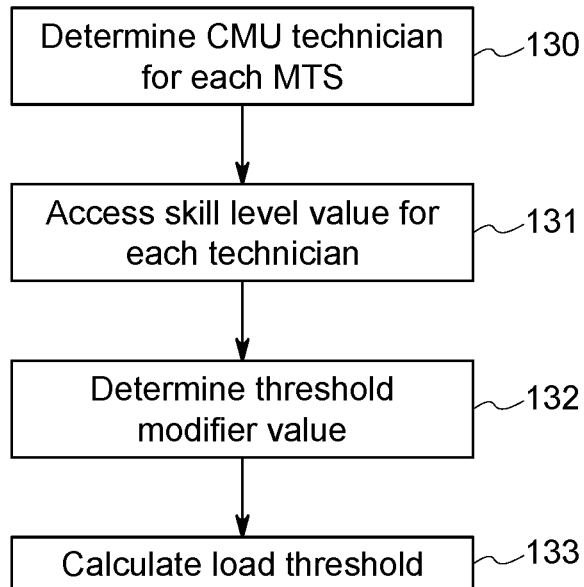

FIG. 6 is a flowchart representing exemplary steps for calculating load threshold to account for technician skill level. Instructions are executed at step 130 to identify the CMU technician 36a-36c assigned to a respective MTS 32a-32c. A skill level value is accessed for each CMU technician at step 131, such as may be comprised in the load threshold schedule 60 discussed above. One or more threshold modifier values are determined at step 132 based on the skill level and the load threshold is calculated at step 133. For example, a default load threshold may be provided and may be multiplied by the threshold modifier value in order to account for the skill level. Other load balancing factors may be accounted for similarly, where a threshold modifier value may be determined at step 132 to account for multiple load balancing factors.

Figure 7:
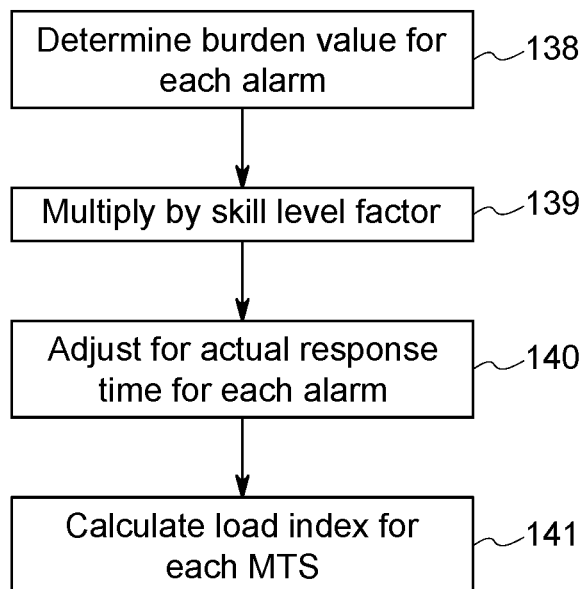

FIG. 7 is a flowchart depicting one embodiment of a load index 72 calculation that accounts for the skill level and/or other load threshold values in the load index calculation, rather than in the load threshold calculation depicted in the example at FIG. 6. A burden value is determined at step 138 and the burden value is multiplied by a skill level factor at step 139. The actual response time for each alarm is determined at step 140 and compared to the expected response duration in the burden value schedule 58. If there is a difference between the actual response time for any one alarm and the expected response duration in the burden value schedule, modified by the skill level factor, then an adjustment is made accordingly. The load index is then calculated for each MTS at step 141 based on the adjusted burden value. Similar adjustments may be made to the expected complexity and expected documentation duration values in the burden value schedule 58 in order to arrive at the load index for each MTS.

Figure 8A:
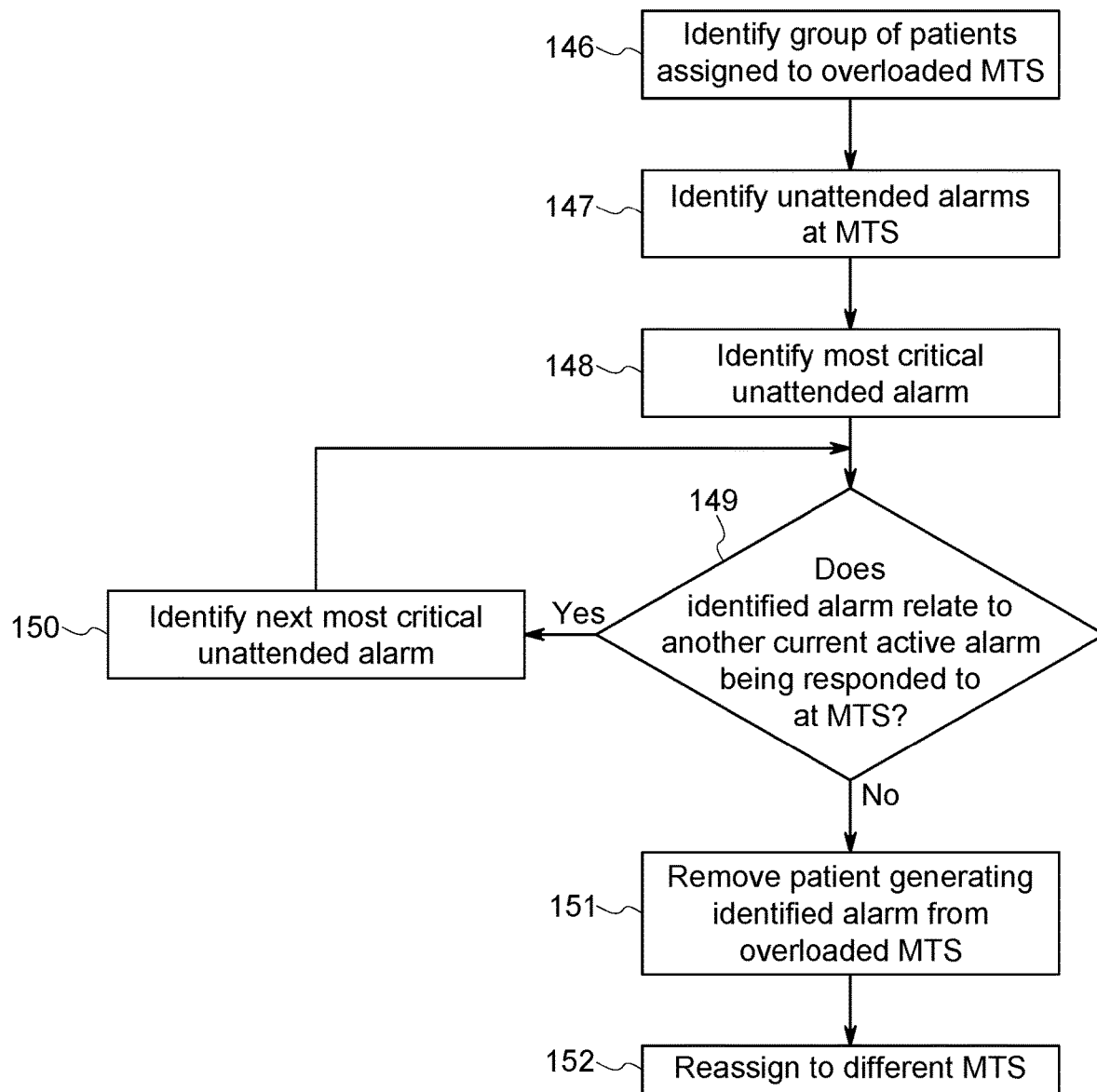

FIG. 8A depicts one embodiment of a method for identifying which patient to remove from an overloaded MTS. A group of patients assigned to an overloaded MTS is identified at step 146. From the group of patients, all unattended alarms for the MTS are identified at step 147, which are active alarms not yet responded to by the CMU technician 36. This finds the active alarms for which the clinician has not yet commenced assessment, such as due to being overloaded and busy responding to other alarms. Of the unattended alarms at the MTS, the most critical unattended alarm at the MTS is identified at step 148. Step 149 is executed to determine whether the identified critical alarm is for the same patient as another active alarm being responded to at the MTS. If so, then the patient will remain at the MTS to be viewed by the same clinician. This configuration may permit efficiency and consistency in response, rather than having multiple CMU technicians 36 responding to different alarms for the same patient 3. Thus, a different alarming patient must be identified and removed from the group of patients assigned to the overloaded MTS. In that instance, step 150 is executed to identify the next most critical unattended alarm at the MTS. The next most critical alarm is again assessed at step 149 to determine whether it is generated by the same patient as an alarm being responded to at the MTS. If not, then the patient associated with the identified alarm at step 149 is removed from the overloaded MTS at step 151 and reassigned to a different MTS at step 152. In other embodiments, the method may identify the oldest pending alarm not yet responded to at the MTS instead of the most critical alarm not yet responded to, and may generally follow the same assessment steps to identify an alarm that can be removed from the overloaded MTS without disrupting the CMU technician or negatively impacting patient care.

Figure 8B:
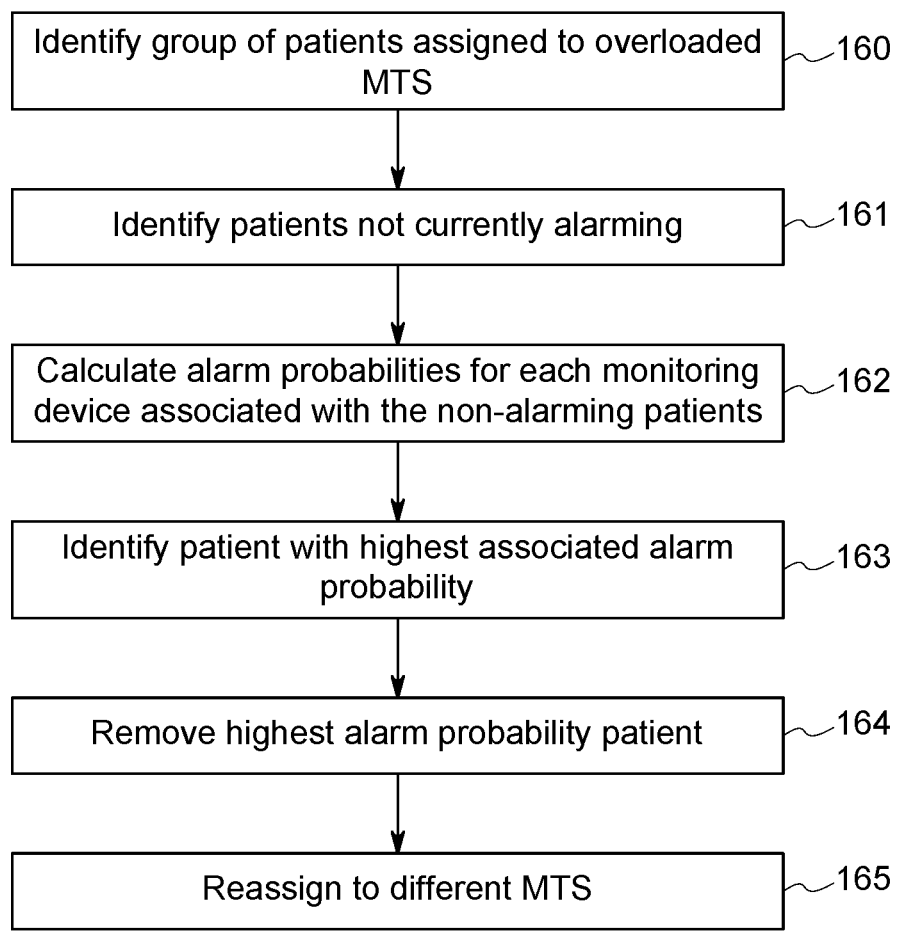

FIG. 8B depicts another embodiment of a method for identifying which patient to remove from an identified overloaded MTS. The group of patients assigned to the overloaded MTS 32 is identified at step 160. Within that group of patients, one or more patients that are not currently alarming are identified at step 161. An alarm probability is then calculated for each monitoring device associated with one of the non-alarming patients at step 162. Of the non-alarming patients, the patient with the highest alarm probability is identified at step 163. The highest alarm probability is then removed from the overloaded MTS at step 164 and is reassigned to a different MTS at step 165. In certain embodiments, the reassignment may be executed automatically so as to provide automated load management, in other embodiments the central computing system may seek approval input from on or more CMU technicians 36 or an administrator prior to executing the reassignment. For example, the assignment management module 42 may be configured to generate a prompt at each of the overloaded and reassigned MTSs 32 seeking approval input prior to executing the reassignment. In another embodiment, the assignment management module 42 may be configured to generate a prompt to a system manager or administrator overseeing assignments, or otherwise seek input from such an individual, prior to executing the reassignment.

Figure 9:
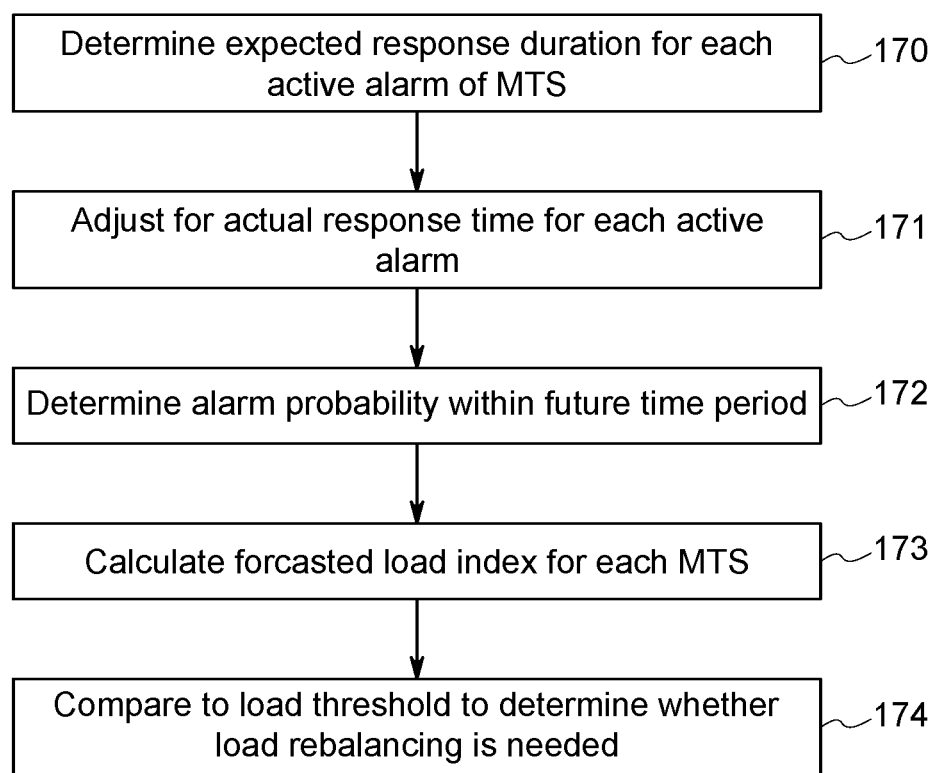

FIG. 9 depicts an exemplary embodiment of method steps for determining a forecasted load index for each MTS 32. Step 170 is executed to determine an expected response duration for each active alarm at a respective MTS. For example, the expected response duration for each active alarm may be the value provided in the burden value schedule 58 based on the response type of each active alarm. The expected response duration for each active alarm may be adjusted at step 171 based on the actual response time for each active alarm, for example if an alarm response is not on track or has already gone over the expected response duration, then the alarm response can be expected to take longer than the expected response duration, and thus the expected end time of the alarm can be adjusted accordingly. The alarm probability is then determined at step 172 for each patient monitoring device associated with each patient in the group of patients assigned to the respective MTS. Various methods for determining alarm probability are described above, such as based on the patient monitoring data being sent by a particular patient monitoring device and/or based on one or more active alarms being generated for a particular patient. A forecasted load index is then calculated for each MTS at step 173 based on the alarm probabilities and the modified expected response durations. The forecasted load index is compared to the load threshold for the respective MTS at step 174 to determine whether load rebalancing is needed. For example, if the forecasted load index exceeds the load threshold then it can be expected that the corresponding MTS is likely to become an overloaded MTS. This situation can be addressed in advance of overloading the MTS by moving one or more patients likely to generate an alarm away from the MTS nearing its load threshold to one or more different MTSs with lower load indexes or forecasted load indexes.

In certain embodiments, a number of MTSs needed may be calculated, and MTSs may be added or removed based on that need. For example, the number of MTSs needed may be determined based on the load indexes 72 and current patient load for the MTSs 32, such as whether the current patient load is manageable (considering completion of any needed or suggested rebalancing and reassignments as described herein) such that the load indexes 72 can be maintained at or sufficiently below their respective thresholds. In certain embodiments, the determination of the number of MTSs 32 needed may also account for the forecasted load index. If the number of MTSs 32 needed is sufficiently greater than the current number of active MTSs 32, then the assignment management module 42 may determine that a new station can be added, or activated, to the CMU 30 (such as by adding an additional CMU technician 36). In this case, the assignment management module provides recommended patient reassignments to the newly activated MTS, thereby rebalancing the loads of the MTSs in the CMU. Conversely, if the current number of patients and alarms is such that the MTSs 32 are operating well below their respective thresholds, then then the assignment management module 42 may determine that one of the MTSs 32 can be removed from operation of the CMU 30 (such as by relieving a CMU technician 36). For example, a determination to add or remove an MTS 32 may be based on a threshold determination based on the load indexes 72 across all MTSs 32. In this case, the remaining patients on the MTS to be deactivated would be reassigned to other MTSs based on recommendations from the assignment management module.

This written description uses examples to disclose the invention, including the best mode, and also to enable any person skilled in the art to make and use the invention. The patentable scope of the invention is defined by the claims and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. A method of centralized patient monitoring management at a centralized monitoring unit (CMU), the method comprising:
   receiving patient monitoring data from multiple patient monitoring devices, each patient monitoring device providing patient monitoring data for one of multiple patients;
   assigning each of the multiple patients to one of at least two monitoring technician stations, each monitoring technician station having at least one display such that the monitoring technician station receives and displays on the at least one display patient monitoring data for each patient in a group of patients assigned thereto and presents alarms for each patient in the group of patients to a CMU technician;
   calculating a load index for each monitoring technician station based on the alarms for each patient in the group of patients assigned to the monitoring technician station, wherein the load index for each monitoring technician station is calculated based on at least one of a number of active alarms at the monitoring technician station, an alarm type of each active alarm at the monitoring technician station, a burden value for the alarm type, a severity of each active alarm at the monitoring technician station, a duration of continuous alarming at the monitoring technician station, an actual response time by the CMU technician to one or more of the active alarms at the monitoring technician station, and a skill level of the CMU technician;
   removing at least one patient from the group of patients assigned to a first monitoring technician station of the at least two monitoring technician stations when the load index for the first monitoring technician station exceeds a load threshold for the first monitoring technician station; and
   reassigning each of the at least one patient removed from the first monitoring technician station to a different one of the at least two monitoring technician stations so as to distribute an overall alarm load for the CMU across all of the at least two monitoring technician stations.

2. The method of claim 1, further comprising identifying one or more low-load monitoring technician stations;
   reassigning each of the at least one patient removed from the first monitoring technician station to one of the one or more low-load monitoring technician stations.

3. The method of claim 2, further comprising determining a respective load threshold for each of the at least two monitoring technician stations.

4. The method of claim 3, further comprising comparing the load index for each monitoring technician station to the load threshold for the respective monitoring technician station to identify the low-load monitoring technician station.

5. The method of claim 3, further comprising determining the load threshold for each of the at least two monitoring technician stations based on at least one of an overall alarm load for the CMU and a skill level of the CMU technician associated with the respective monitoring technician station.

6. The method of claim 1, further comprising:
   calculating an alarm probability within a future time period for each monitoring device associated with a patient in the group of patients assigned to the first monitoring technician station; and
   identifying the at least one patient removed from the first monitoring technician station as one or more patients that are not currently alarming and are associated with a highest alarm probability.

7. The method of claim 1, further comprising:
   identifying one or more critical alarms for patients assigned to the first monitoring technician station; and
   removing the at least one patient based on the identified critical alarms.

8. The method of claim 1, further comprising:
   identifying one or more unattended alarms for patients assigned to the first monitoring technician station; and
   removing the at least one patient based on the identified unattended alarms.

9. The method of claim 1, wherein the load index for each monitoring technician station is calculated based on at least two of a number of active alarms at the monitoring technician station, an alarm type of each active alarm at the monitoring technician station, a burden value for the alarm type, a severity of each active alarm at the monitoring technician station, a duration of continuous alarming at the monitoring technician station, an actual response time by the CMU technician to one or more of the active alarms at the monitoring technician station, and a skill level of the CMU technician.

10. The method of claim 1, wherein the reassigning each of the at least one patient removed from the first monitoring technician station to a different one of the at least two monitoring technician stations includes moving a responding clinician assignment such that the responding clinician assignment for the removed patient is maintained.

11. The method of claim 1, further comprising automatically assigning a new patient to one of the at least two monitoring technician stations based on the load indexes.

12. The method of claim 1, further comprising determining a number of monitoring technician stations needed based on the load indexes for the at least two monitoring technician stations; and
   adding or removing a monitoring technician station based on the number of monitoring technician stations needed.

13. The method of claim 1, further comprising operating the different one of the at least two monitoring technician stations to receive and display the patient monitoring data for and present the alarms for the at least one patient removed from the first monitoring technician station.

14. A centralized monitoring unit (CMU) receiving patient monitoring data from multiple patient monitoring devices, each patient monitoring device providing patient monitoring data for a respective one of multiple patients, the CMU comprising:

at least two monitoring technician stations, each monitoring technician station having at least one display and configured to:

receive and display on the at least one display patient monitoring data for each patient in a group of patients assigned thereto;

present alarms for each patient in the group of patients to a CMU technician;

wherein each of the multiple patients for which patient monitoring data is received at the CMU is assigned to one of the at least two monitoring technician stations;

an assignment management module executable by a processing system to:

calculate a load index for each monitoring technician station wherein the load index for each monitoring technician station is calculated based on at least one of a number of active alarms at the monitoring technician station, an alarm type of each active alarm at the monitoring technician station, a burden value for the alarm type, a severity of each active alarm at the monitoring technician station, a duration of continuous alarming at the monitoring technician station, an actual response time by the CMU technician to one or more of the active alarms at the monitoring technician station, and a skill level of the CMU technician;

remove at least one patient of the multiple patients from assignment to a first monitoring technician station of the at least two monitoring technician stations based when the load index for the first monitoring technician station exceeds a load threshold for the first monitoring technician station; and reassign each of the at least one patient removed from the first monitoring technician station to a different one of the at least two monitoring technician stations.

15. The CMU of claim 14, wherein each of the at least patient removed from the first monitoring technician station is assigned to the different monitoring technician station based on the load index for the different monitoring technician station so as to distribute an overall alarm load for the CMU across all of the at least two monitoring technician stations.

16. The CMU of claim 14, wherein the assignment management module is further executable to determine that the load index for the first monitoring technician station is greater than load indexes for other ones of the at least two monitoring technician stations prior to removing the at least one patient.

17. The CMU of claim 14, wherein the load threshold for each of the at least two monitoring technician stations is determined based on a skill level of the CMU technician at the respective monitoring technician station.

18. The CMU of claim 14, wherein the load threshold for each of the at least two monitoring technician stations is determined based on an overall alarm load for the CMU.

19. The CMU of claim 14, wherein the assignment management module is further executable to:

calculate an alarm probability within a future time period for each patient monitoring device associated with a patient in the group of patients assigned to the first monitoring technician station;

identify one or more patients that are not currently alarming and are associated with a highest alarm probability as the at least one patient removed from the first monitoring technician station.

20. The CMU of claim 14, wherein the assignment management module is further executable to:

identify one or more critical alarms for patients assigned to the first monitoring technician station; and remove the at least one patient based on the identified critical alarms.

21. The CMU of claim 14, wherein the assignment management module is further executable to:

identify one or more unattended alarms for patients assigned to the first monitoring technician station; and remove the at least one patient based on the identified unattended alarms.

22. The CMU of claim 14, wherein the load index for each monitoring technician station is calculated based on at least two of a number of active alarms at the monitoring technician station, an alarm type of each active alarm at the monitoring technician station, a burden value for the alarm type, a severity of each active alarm at the monitoring technician station, a duration of continuous alarming at the monitoring technician station, an actual response time by the CMU technician to one or more of the active alarms at the monitoring technician station, and a skill level of the CMU technician.

23. The CMU of claim 14, wherein each of the at least one patient removed from the first monitoring technician station is reassigned to the different one of the at least two monitoring technician stations such that the different one of the at least two monitoring technician stations receives and displays on the at least one display the patient monitoring data for and presents the alarms for the at least one patient removed from the first monitoring technician station.

* * * * *